United States Patent [19]

Chono et al.

[11] 4,122,269
[45] Oct. 24, 1978

[54] 1,3,6-TRIS(4,6-DIAMINO-1,3,5-TRIAZINE-2-YL)HEXANE

[75] Inventors: Masazumi Chono, Yokohama; Hideo Ai, Fuji; Michihiro Aboshi; Yoshikazu Suda, both of Tokyo; Naoji Yoshii, Yokohama, all of Japan

[73] Assignee: Asahi Kasei Kogyo Kabushiki Kaisha, Osaka, Japan

[21] Appl. No.: 819,134

[22] Filed: Jul. 26, 1977

[30] Foreign Application Priority Data

Jul. 28, 1976 [JP] Japan .................................. 51-89064
Aug. 11, 1976 [JP] Japan .................................. 51-94943

[51] Int. Cl.$^2$ .......................................... C07D 251/48
[52] U.S. Cl. ............................ 544/207; 260/45.8 NT
[58] Field of Search ........................................... 544/207

[56] References Cited

U.S. PATENT DOCUMENTS 2,684,366  7/1954  Simons ............................... 260/249.9

FOREIGN PATENT DOCUMENTS 4,722,427  10/1972  Japan.
4,722,428  10/1972  Japan.

Primary Examiner—John M. Ford
Attorney, Agent, or Firm—Armstrong, Nikaido, Marmelstein & Kubovcik

[57] ABSTRACT 1,3,6-Tris(4,6-diamino-1,3,5-triazine-2-yl)hexane, and a flame retardant resin composition comprising (A) about 5 to about 100 parts by weight of 1,3,6-tris(4,6-diamino-1,3,5-triazine-2-yl)hexane and (B) 100 parts by weight of a thermosetting resin or a thermoplastic resin.

1 Claim, 2 Drawing Figures

1,3,6-TRIS(4,6-DIAMINO-1,3,5-TRIAZINE-2-YL)HEXANE

BACKGROUND OF THE INVENTION

1. Field of the Invention

This invention relates to a novel triguanamine compound. More particularly, it relates to 1,3,6-tris(4,6-diamino-1,3,5-triazine-2-yl)hexane which is useful as a flame retardant and a flame retardant resin composition comprising the above described compound.

2. Description of the Prior Art

It is known according to U.S. Pat. No. 2,684,366 that guanamine compounds can be prepared by reacting a nitrile compound with dicyandiamide.

SUMMARY OF THE INVENTION

This invention provides 1,3,6-tris(4,6-diamino-1,3,5-triazine-2-yl)-hexane (hereinafter referred to "triguanamine") which is a novel compound and useful as a flame retardant, and a flame retardant resin composition comprising the above described compound.

BRIEF DESCRIPTION OF THE ACCOMPANYING DRAWINGS

DETAILED DESCRIPTION OF THE INVENTION

Figure 1:
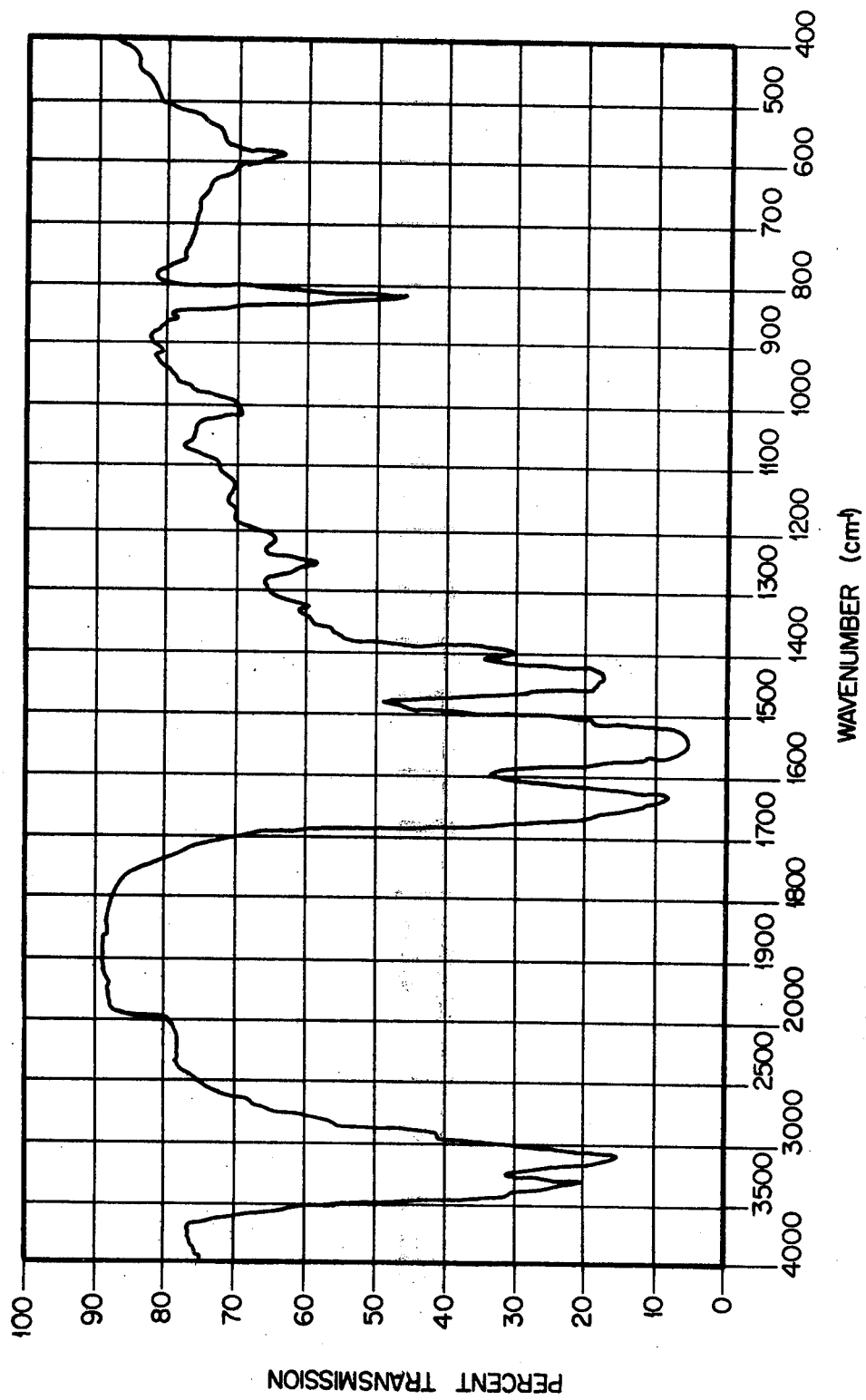
FIG. 1 shows the infrared absorption spectrum of 1,3,6-tris(4,6-diamino-1,3,5-triazine-2-yl)hexane according to the present invention.

The triguanamine according to the present invention can be obtained by reacting 1,3,6-tricyanohexane with dicyandiamide in the presence of a basic catalyst.

The 1,3,6-tricyanohexane which is employed for preparing the triguanamine of this invention is a known compound and can be obtained by the electro-reductive reaction of acrylonitrile, and has hardly been used industrially.

The amount of the dicyandiamide which can be used in the preparation of the triguanamine of this invention is theoretically 3 molar times based on the 1,3,6-tricyanohexane, and typically from about 3.1 to about 3.3 molar times based on the 1,3,6-tricyanohexane.

Exemplary basic catalysts which can be used in the preparation of the triguanamine according to this invention include alcoholates of a metal of Group Ia, IIa or IIIa of the Periodic Table such as sodium methylate, sodium ethylate, sodium β-methoxyethylate, potassium methylate, potassium ethylate, magnesium diethylate, aluminum triethylate, etc.; hydroxides of a metal of Group Ia, IIa or IIIa of the Periodic Table such as sodium hydroxide, potassium hydroxide, calcium hydroxide, barium hydroxide, aluminum hydroxide, etc.; and tertiary amino compounds such as trimethylamine, triethylamine, triethylenediamine, dimethyl octylamine, 1,8-diaza-dicyclo(5,4,0)undecene-7, triphenylamine, hexamethylenetetramine, etc. Of these compounds, sodium or potassium alcoholates and sodium or potassium hydroxides are preferably employed.

The amount of the catalyst preferably ranges from about 0.05 to about 2 moles per mole of 1,3,6-tricyanohexane used from the standpoint of its economy and the yield of the product.

In the preparation of the triguanamine according to this invention, usually a reaction medium is employed.

Exemplary reaction media include dialkyl sulfoxides such as dimethyl sulfoxide, diethyl sulfoxide, etc.; dialkylformamides such as dimethylformamide, diethylformamide, etc.; and alcohols having a boiling point above about 100° C such as β-methoxy ethanol, β-ethoxy ethanol, β-butoxy ethanol, β-methoxy propanol, β-methoxy butanol, β-ethoxy butanol, n-amyl alcohol, sec-amyl alcohol, tert-amyl alcohol, isoamyl alcohol, benzyl alcohol, etc. Of these compounds dimethyl sulfoxide and diethyl sulfoxide are especially preferred.

The amount of the reaction medium preferably ranges from about 500 g to about 3,000 g per mole of 1,3,6-tricyanohexane used from the standpoint of its economy and the yield of the product.

The above described basic catalyst is added to the reaction medium together with the starting materials of this invention. When the basic catalyst is hard to dissolve in the reaction medium, it is preferred that the catalyst is previously dissolved or dispersed in a medium (hereinafter referred to "dispersion medium") which is miscible with the reaction medium and easy to dissolve or disperse therein the catalyst, and then the resulting solution or dispersion is added to the reaction medium from the standpoint of an improvement on reaction yields.

The dispersion media are suitably selected depending on the catalyst chosen and the reaction medium chosen, and typically includes water, alcohols having 1 to 4 carbon atoms such as methanol, ethanol, etc. and polyols such as glycerine, etc. The concentration of the catalyst based on the dispersion medium is not particularly limited but generally it ranges from about 5% by weight to about 30% by weight.

The reaction temperature in the preparation of the triguanamine according to this invention is typically from about 70° C to about 200° C and a preferred range is from about 100° C to about 170° C. When the temperature is above about 200° C, disadvantageously the decomposition of 1,3,6-tricyanohexane and dicyandiamide as the starting materials vigorously occurs.

The reaction completes for about 2.5 hours but generally the reaction is conducted for about 3 hours to about 7 hours.

The reaction pressure in the preparation of the triguanamine according to this invention may be either atmospheric pressure, a reduced pressure or a pressure above atmospheric, but atmospheric pressure is preferred for practical purposes. In order to prevent the reaction product from discoloring and improve the yield of the product, it is preferred that the reaction is conducted in an inactive gas atmosphere such as nitrogen gas.

The purification of the triguanamine of this invention thus obtained can be conducted by cooling the reaction solution to temperatures below about 50° C to precipitate the reaction product, separating the precipitate by filtration, recrystallizing the resulting product from a solvent medium such as dimethyl sulfoxide, dimethylformamide, etc. and/or washing the product with water.

The general properties of 1,3,6-tris(4,6-diamino-1,3,5-triazine-2-yl)-hexane are as follows:

Molecular formula: $C_{15}H_{23}N_{15}$
Molecular weight: 413.5
Appearance: White powder Specific gravity (25° C): 1.37
 (Gas pycnometer method; Kagaku Kojo, Vol. 17, No. 6, p. 30, Nikkan Kogyo Shinbun)
Melting point: 187° C
 (Differential thermal analysis method; Kagakuno Ryoiki, Special No. "Thermal property measurement and differential thermal analysis 78", p. 124, 1968, Nankodo)
Solubility
 Water: Sparingly soluble
 Alcohols: ditto
 (methanol, ethanol, butanols, etc.)
 Ketones: ditto
 (acetone, methyl ethyl ketone, etc.)
 Dixanes: ditto
 (1,3-dioxane, 1,4-dioxane, etc.)
 Dialkyl sulfoxides: Slightly soluble
 (diethyl sulfoxide, dimethyl sulfoxide, etc.)

The reaction product thus obtained can be identified by elementary analysis, quantitative analysis of primary amine and by its infrared absorption spectrum and ultraviolet absorption spectrum.

The triguanamine of this invention is useful as a flame retardant and by incorporating the triguanamine with thermoplastic resins or thermosetting resins, there can be obtained flame retardant resin compositions. When the triguanamine of this invention is used as a flame retardant for resins, the resin compositions containing the triguanamine have good flame retardation, and do not evolve any poisonous gas at the time of burning. Further, hardly any bleeding of the triguanamine in molding the resin compositions to shaped articles and from the shaped articles is observed.

The thermoplastic resins and thermosetting resins which can be used in the practice of this invention are not particularly limited. The flame retardant resin compositions of this invention can be obtained by mixing the triguanamine of this invention with a variety of thermoplastic resins and thermosetting resins.

The thermoplastic resins which can be used in the practice of this invention include polyamide resins such as nylon 6, nylon 66, nylon 610, nylon 612 and copolymers thereof; linear saturated aromatic polyester resins such as polyethylene terephthalate, polytetramethylene terephthalate and polyhexamethylene terephthalate; polyphenylene oxide resins and mixtures of polyphenylene oxide and polystyrene; polyolefin resins such as polyethylene, polypropylene and polystyrene; polyacrylate resins such as polymethyl acrylate and polymethyl methacrylate; styrene-butadiene copolymers and acrylonitrile-butadiene-styrene copolymers; polycarbonate resins whose dioxane component is Bisphenol-A or 1,1-bis(4-hydroxyphenyl)cyclohexane; polyacetal homopolymers and copolymers.

The thermosetting resins used include unsaturated polyester resins obtained from a mixture of polyester prepolymers prepared by reacting glycols such as ethylene glycol, tetramethylene glycol, etc. with unsaturated dicarboxylic acids such as fumaric acid, maleic acid, etc. and cross-linkable monomers, and obtained from diallyl phthalate, diallyl terephthalate or diallyl-2,6-naphthalene dicarboxylate; polyurethane resins obtained by reacting polyisocyanates such as hexamethylene diisocyanate, tolylene diisocyanates, 4,4'-diphenylmethane diisocyanate and derivatives thereof with polyhydroxyl compounds such as (1) polyester polyols including polyethylene adipate glycol, polyethylene phthalate glycol and polyester polyols obtained from adipic acid, etc. and trimethylol propane, etc., (2) polyether polyols such as polyoxyethylene polyol, polyoxypropylene polyol, polyoxypropylene polyol, etc, and (3) acryl polyols; and epoxy resins obtained from a condensate of a polyhydroxyl phenol such as Bisphenol A, etc. and epichlorohydrin etc., and a hardening agent such as organic acids, organic acid anhydrides.

The amount of the triguanamine of this invention which can be incorporated with thermosetting or thermoplastic resins may vary depending upon the flame retardation of resin compositions desired, the shape of molded articles, the presence or absence of flame retardant auxiliary agents, etc., and typically ranges from about 5 to about 100 parts by weight based on 100 parts by weight of the thermosetting or thermoplastic resins. A preferred amount ranges from about 7 to about 40 parts by weight based on 100 parts by weight of the thermosetting or thermoplastic resins. When the amount of the triguanamine is more than about 100 parts by weight, the processability and properties of molded articles are deteriorated.

The flame retardant resin compositions according to this invention may additionally contain such conventional phosphorus type or halogen type flame retardants; flame retardant auxiliary agents such as antimony trioxide, barium metaborate, zirconium dioxide, iron oxides, zinc borate, etc.; third components such as delustering agents, pigments, dyes, stabilizers, plasticizers and dispersing agents, etc.; and internal reinforcing agents such as glass fibers, carbon fibers, calcined clay, calcium carbonate, etc. as do not detract from their desirable characteristics.

For the purpose of uniformly incorporating the triguanamine of this invention with thermosetting or thermoplastic resins, any conventional methods such as solution mixing methods, dry blend methods, melt mixing methods may be conveniently employed. Of these methods, melt mixing methods are preferred in obtaining flame retardant resin compositions in order for the triguanamine to fully exhibit its flame retardation. With regard to thermoplastic resins, pellets or powder of the resins are mixed with the triguanamine at room temperature, and subsequently the resulting mixture is molded by a melt molder such as an extruder. Alternatively, the mixture is pelletized, followed by melt molding the resulting pellets to give shaped articles. Also, a resin composition containing the triguanamine in a high concentration is firstly prepared, and the resin composition is secondly melt mixed with the corresponding ordinary resin, followed by molding the melt mix.

With regard to thermosetting resins it is preferred that the triguanamine is added to and mixed with a dope or compound of the monomers or prepolymer with or without an internal reinforcing agent before hardening, followed by hardening the resulting mixture.

The present invention will now be illustrated in greater detail by the following Examples.

EXAMPLE 1

161 g (1 mole) of 1,3,6-tricyanohexane and 277.2 g (3.3 moles) of dicyandiamide were added to 750 g of dimethyl sulfoxide as the reaction medium, followed by further addition of 68 g (1 mole) of sodium methylate as the catalyst. The mixture was stirred under heating at 130° C for 3 hours in a nitrogen atmosphere. After completion of the reaction the reaction mixture was cooled to 25° C to precipitate the reaction product, followed by separating the crude reaction product by filtration. Purification was conducted by dissolving the crude product in excess amount of dimethyl sulfoxide at 135° C and then precipitating the product by cooling. After repeating this procedure 5 times, 292 g of 1,3,6-tris(4,6-diamino-1,3,5-triazine-2-yl)hexane as a white powder were obtained.

Elementary analysis for $C_{15}H_{23}N_{15}$:
 Calculated (%): C 43.57, H 5.61, N 50.82
 Found (%): C 43.55, H 5.65, N 50.71

Infrared absorption spectrum (KBr tablet method):
 In the infrared absorption spectrum as shown in FIG. 1, the absorptions due to an aminotriazine ring are observed at 3100, 1640, 1540, 1460 and 1430 $cm^{-1}$, and the absorption at around 2240 $cm^{-1}$ due to a nitrile group which can be observed in the infrared absorption spectrum of 1,3,6-tricyanohexane is not observed.

Figure 2:
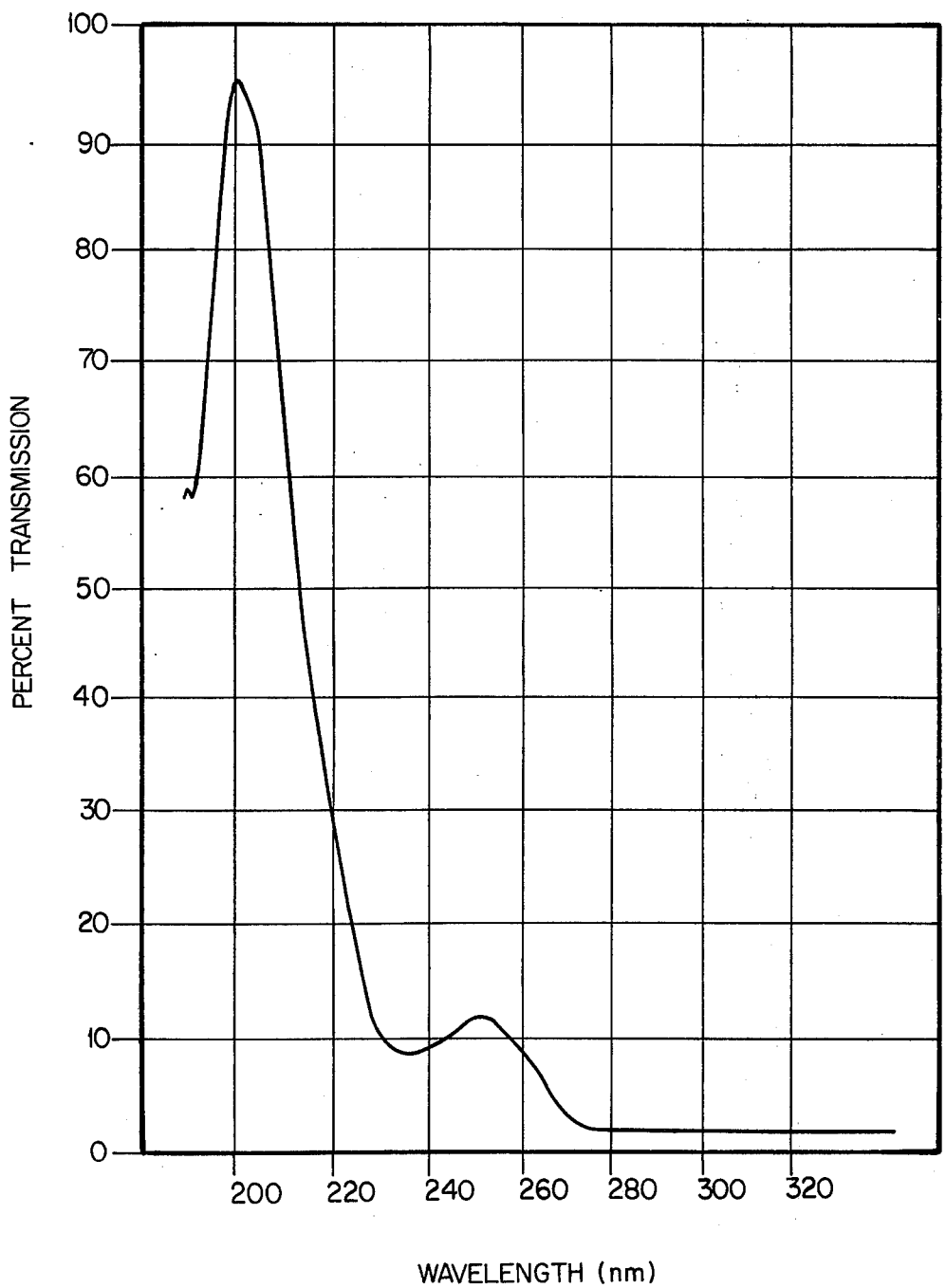
FIG. 2 shows the ultraviolet absorption spectrum of a neutral aqueous solution of 1,3,6-tris(4,6-diamino-1,3,5-triazine-2-yl)hexane according to the present invention.

Ultraviolet absorption spectum:
 In the ultraviolet absorption spectrum (neutral solution; sample: 5 γ/1ml) as shown in FIG. 2, the absorptions due to the conjugated double bond in triazine ring are observed at 202 nm and 252 nm. Quantitative analysis of primary amine:

0.413 g (0.001 mole) of the sample was dissolved in 20 ml of a 0.5 N hydrochloric acid solution and the resulting solution was subjected to back titration with 0.5 N sodium hydroxide using Methyl orange as an indicator. The amount of the 0.5 N sodium hydroxide necessary for neutralizing the hydrochloric acid solution was 8.3 ml, and accordingly the amount of amino group became 0.00585 mole. Thus, it was confirmed that the reaction product had about 6 amino groups per molecule.

EXAMPLE 2

Following the same procedures and conditions as described in Example 1 except for those as set forth in Table I, 1,3,6-tris(4,6-diamino-1,3,5-triazine-2-yl)hexane was prepared.

The reaction products were identified as the same reaction product as in Example 1 by the same methods as in Example 1.

Table I

| Run No. | 1,3,6-Tricyanohexane [g(mole)] | Dicyandiamide [g(mole)] | Catalyst [g(mole)] | Reaction Medium (g) | Dispersion Medium (g) | Reaction Temperature (° C) | Reaction Time (hour) | Yield (g) |
|---|---|---|---|---|---|---|---|---|
| 1 | 161 (1.0) | 277.2 (3.3) | KOH 56 (1.0) | β-Methoxybutanol 750 | Glycerin 164 | 125 | 5 | 265 |
| 2 | " | " | $N(C_6H_5)_3$ 20 (0.12) | Dimethyl sulfoxide 750 | — | 115 | 7 | 225 |
| 3 | " | " | $C_2H_5ONa$ 13.6 (0.2) | " | — | 130 | 3 | 173 |
| 4 | " | " | $C_2H_5ONa$ 68 (1.0) | " 1500 | — | " | " | 322 |
| 5 | " | 210 (2.5) | " | " 750 | — | " | " | 157 |
| 6 | " | 319.2 (3.8) | " | " | — | " | " | 334 |
| 7 | " | 277.2 (3.3) | " | " | — | 90 | " | 210 |
| 8 | " | " | " | " | — | 170 | " | 232 |
| 9 | " | " | $CH_3ONa$ 54 (1.0) | " | — | 130 | " | 251 |
| 10 | " | " | $Ba(OH)_2$ 34.2 (0.2) | Dimethyl sulfoxide 750 | $H_2O$ 300 | " | " | 322 |
| 11 | " | " | Al(OH) 39 (0.5) | " | " 400 | " | " | 157 |
| 12 | " | " |  56 (0.5) | " | — | " | " | 334 |
| 13 | " | " | $N(C_2H_5)_3$ 50.5 (0.5) | " | — | " | " | 210 |
| 14 | " | " | $(CH_3)_2NC_8H_{15}$ 47.1 (0.3) | " | — | " | " | 232 |
| 15 | " | " | $C_2H_5ONa$ 68 (1.0) | Diethyl sulfoxide 750 | — | " | " | 295 |
| 16 | " | " | " | β-Methoxypropanol 750 | — | " | " | 67 |
| 17 | " | " | " | Isoamyl alcohol 750 | — | " | " | 43 |
| 18 | " | " | " | Benzyl alcohol 75⁻ | — | " | " | 30 |

EXAMPLE 3

The triguanamine obtained in Example 1 was mixed with a variety of the resins in a desired amount as set forth in Table II and each of the resulting mixtures was molded into a shaped article and the shape article was subjected to the vertical burning test according to UL Standard Subject 94. The results are shown in Table II.

In Table II, the resins used are shown below. With respect to the thermoplastic resins (1) to (16), dry pellets of each of the resins and the triguanamine were mixed and the resulting mixture was melt mixed at 270° C as for the resins (1) to (12), (14) and (16), 220° C as for the resin (13) and 200° C as for the resin (15) by a conventional extruder (made by Tanabe Plastic Machinery Co.; 40 mm vent type extruder), extruded, pelletized, followed by preparing a shaped article having a dimension of 127 mm × 12.7 mm × 0.8 mm (1/32") for burning test using an injection molder.

With regard to the thermosetting resins (17) to (20), the method for preparing a shaped article for burning test is given with each of the resins.

(1) Nylon 6: made by Asahi Chemical Industry Co.; injection molding grade
(2) Nylon 66: made by Asahi Chemical Industry Co.; injection molding grade
(3) Nylon 610: made by Toray Industries Inc.; trademark "CM 2001"
(4) Nylon 11: made by Nihon Rilson Co.; trademark "Rilson BMN"
(5) Nylon 12: made by Toray Industries Inc.; trademark "CM 5001"
(6) Nylon 6 nylon 66 random copolymer resin: obtained from ε-caprolactam : hexamethylene diamine : adipic acid = 10 : 45 : 45 (mole ratio), relative viscosity (JIS-K 6810) = 2.0 (98% $H_2SO_4$, 25° C)
(7) Nylon 6 nylon 66 blend resin : a blend of the above described nylon 6 and nylon 66 in a weight ratio of 1 : 1
(8) Polyethylene terephthalate : intrinsic viscosity = 0.64 (o-chlorophenol, 35° C)
(9) Polytetramethylene terephthalate: made by Akzo N.V.; injection molding grade; intrinsic viscosity = 1.2 (o-chlorophenol, 35° C)
(10) Polystyrene: made by Asahi-Dow Ltd.; injection molding grade; melt flow rate = 7.5 g/10 minutes (190° C, 2.16 Kg)
(11) Acrylonitrile-butadiene-styrene copolymer: made by Asahi-Dow Ltd.; trademark "STYLAC 100"; melt flow rate = 20 g/10 minutes (200° C, 21.6 Kg)
(12) Modified polyphenylene oxide resin: made by General Electric Co.; trademark "NORYL 731"; a mixture of polyphenylene oxide and polystyrene in a weight ratio of about 1 : 1.
(13) Polymethyl methacrylate resin: reduced viscosity = 0.051 (chloroform 3 g/l, 20° C)
(14) Polycarbonate resin: made by Teijin Ltd.; trademark "PANLITE L"; Bisphenol A type polycarbonate
(15) Polyacetal resin: made by E. I. Du Pont de Nemours & Co.; injection molding grade; polyoxymethylene homopolymer; melt index = 13 (190° C, 2.16 Kg)
(16) Polyethylene: made by Asahi Chemical Industry Co.; injection molding grade; melt index = 6 (190° C, 2.16 Kg)
(17) Thermosetting polyester resin: prepared by polycondensing maleic anhydride and ethylene glycol in a mole ratio of 1 : 1 at 140° C in a nitrogen atmosphere for 5 hours to give polyethylene maleate, mixing the resulting polyethylene maleate, styrene, benzoyl peroxide and dimethylaniline in a weight ratio of 70 : 30 : 2 : 0.1, further adding a prescribed amount of the triguanamine to the mixture, charging the resulting mixture between two glass sheets, heating the assembly at 60° C for 24 hours and then at 100° C for 3 hours to give a hardened shaped article and cutting the article to a dimension of 127 mm × 12.7 mm × 0.8 mm (1/32") for burning test.
(18) Diallyl phthalate resin: prepared by heating diallyl phthalate to a temperature between 60° C and 80° C, dissolving therein a prescribed amount of the triguanamine, further adding 2% by weight of dicumyl peroxide to the mixture, charging the resulting mixture between two glass sheets, heating the assembly at 80° C for 2 days to give a hardened shaped article and cutting the article to the same dimension as described in (17).
(19) Polyurethane resin: prepared by mixing tolylene diisocyanate consisting of 2,4-tolylene diisocyanate and 2,6-tolylene diisocyanate in a rate of 80 : 20 with polyethylene glycol having a number average molecular weight of 600 in a mole ratio of isocyanate group to hydroxyl group of 1 : 1, further adding thereto a prescribed amount of the triguanamine, charging the resulting mixture between two glass sheets, leaving the assembly to stand at room temperature for one week to give a hardened shaped article and cutting the article to the same dimension as described in (17).
(20) Epoxy resin: prepared by mixing Bisphenol A type epoxy resin having a number average molecular weight of 560 with hexahydrophthalic anhydride in a weight ratio of 100 : 55, further adding thereto a prescribed amount of the triguanamine, charging the resulting mixture between two glass sheets, heating the assembly at 120° C for 5 hours to give a shaped article and cutting the article to the same dimension as described (17).

Table II

| Run No. | Resin | Triguanamine (g/100 g of resin) | Bleeding of Flame Retardant in Molding | Bleeding of Flame Retardant from Shaped Article | Color of Shaped Article | UL Standard Subject 94 Vertical Burning Test |
|---|---|---|---|---|---|---|
| 1 | Nylon 6 [1] | 18 | None | None | White | V-0 |
| 2 | " | 25 | " | " | " | " |
| 3 | Nylon 66 [2] | 18 | " | " | " | " |
| 4 | Nylon 610 [3] | " | " | " | " | " |
| 5 | Nylon 11 [4] | " | " | " | " | " |
| 6 | Nylon 12 [5] | " | " | " | " | " |
| 7 | Nylon 6 nylon 66 random copolymer resin [6] | " | " | " | " | " |
| 8 | Nylon 6 nylon 66 blend resin [7] | " | " | " | " | " |
| 9 | Polyethylene terephthalate [8] | " | " | " | " | V-0 |
| 10 | " | 25 | " | " | " | " |
| 11 | Polytetramethylene terephthalate [9] | 18 | " | " | " | " |
| 12 | Polystyrene [10] | " | " | " | " | V-2 |
| 13 | Acrylonitrile-butadiene-styrene copolymer [11] | 33 | " | " | " | V-0 |
| 14 | Modified polyphenylene oxide resin [12] | 25 | None | None | White | V-1 |
| 15 | Polymethyl methacrylate resin [13] | 33 | " | " | " | V-0 |
| 16 | Polycarbonate resin [14] | " | " | " | " | V-1 |
| 17 | Polyacetal resin [15] | 67 | " | " | " | " |

Table II-continued

| Run No. | Resin | Triguanamine (g/100 g of resin) | Bleeding of Flame Retardant in Molding | Bleeding of Flame Retardant from Shaped Article | Color of Shaped Article | UL Standard Subject 94 Vertical Burning Test |
|---|---|---|---|---|---|---|
| 18 | Polyethylene[16] | 25 | " | " | " | " |
| 19 | Thermosetting polyester resin[17] | 18 | " | " | " | V-0 |
| 20 | Diallyl phthalate resin[18] | " | " | " | " | V-1 |
| 21 | Polyurethane resin[19] | 33 | " | " | " | " |
| 22 | Epoxy resin[20] | 25 | " | " | " | V-0 |

COMPARATIVE EXAMPLE 1

For comparison, the shaped articles of a variety of the resins which did not contain the triguanamine and those of nylon 6 and polyethylene terephthalate which contained a conventional flame retardant together with or without antimony trioxide as a flame retardant auxiliary agent were subjected to the same burning test as in Example 3. The results are shown in Table III. The resins employed and the methods for preparing the shaped articles were the same as in Example 3.

As is clear from the results given in Tables II and III, the resin compositions according to the present invention have superior flame retardation. Further, the bleeding of a flame retardant in molding and from shaped articles obtained and the discoloring of shaped articles which are disadvantages with regard to conventional flame retardants have remarkably improved.

Table III

| Run No. | Resin | Flame Retardant (g/100 g of resin) | $Sb_2O_3$ as Flame Retardant Auxiliary Agent (weight %) | Bleeding of Flame Retardant in Molding | Bleeding of Flame Retardant from Shaped Article | Color of Shaped Article | UL Standard Subject 94 Vertical Burning Test |
|---|---|---|---|---|---|---|---|
| 1 | Nylon 6[1] | — | — | None | None | White | HB |
| 2 | " | Melamine 18 | — | ⊚ | O | " | V-0 |
| 3 | " | Hexabromobenzene 18 | 3 | O | Δ | Yellow | " |
| 4 | " | 6-(2',3',4',5'-Tetrabromophenyl)-1,2,3,4,7,7-hexachlorobicyclo-[2,2,1]heptene-2 18 | 5 | O | Δ | Brown | " |
| 5 | Nylon 66[2] | — | — | None | None | White | V-2 |
| 6 | Nylon 610[3] | — | — | " | " | " | " |
| 7 | Nylon 11[4] | — | — | " | " | " | HB |
| 8 | Nylon 12[5] | — | — | " | " | " | " |
| 9 | Nylon 6 nylon 66 random copolymer resin[6] | — | — | " | " | " | V-2 |
| 10 | Nylon 6 nylon 66 blend resin | — | — | " | " | " | " |
| 11 | Polyethlene terephthalate[8] | — | — | " | " | " | " |
| 12 | " | Melamine 18 | — | ⊚ | O | " | V-0 |
| 13 | " | Hexabromobenzene 18 | 3 | O | Δ | " | " |
| 14 | " | 2,3,4,5,2',3',4',5'-Octabromobiphenyl 18 | 5 | Δ | Δ | " | " |
| 15 | Polytetramethylene terephthalate[9] | — | — | None | None | " | V-2 |
| 16 | Polystyrene[10] | — | — | " | " | " | HB |
| 17 | Acrylonitrile-butadiene-styrene-copolymer[11] | — | — | " | " | " | " |
| 18 | Modified polyphenylene oxide resin[12] | — | — | " | " | " | " |
| 19 | Polymethyl methacrylate resin[13] | — | — | " | " | " | " |
| 20 | Polycarbonate resin[14] | — | — | " | " | " | " |
| 21 | Polyacetal resin[15] | — | — | " | " | " | " |
| 22 | Polyethylene[16] | — | — | " | " | " | " |
| 23 | Thermosetting polyester resin[17] | — | — | " | " | " | " |
| 24 | Diallyl phthalate resin[18] | — | — | " | " | " | " |
| 25 | Polyurethane resin[19] | — | — | " | " | " | " |
| 26 | Epoxy resin[20] | — | — | " | " | " | V-1 |

Note: ⊚ Bleeding occurred remarkably.
O Bleeding occurred.
Δ Bleeding occurred slightly.

EXAMPLES 4 TO 7 and

COMPARATIVE EXAMPLES 2 TO 4

The same dry pellets of nylon 66 as in Example 2, Run No. 3 were mixed with the triguanamine obtained in Example 1 in a ratio as set forth in Table IV, and the resulting mixture was melt mixed and molded in the same manner as in Example 2 to give a shaped article having a dimension of 127 mm × 12.7 mm × 0.8 mm (1/32") for burning test and a shaped article having a dimension of 50.8 mm × 12.7 mm × 3 mm which was then notched for Izod impact strength test. These articles thus obtained were subjected to the vertical burning test according to UL Standard Subject 94 and the Izod impact strength test according to ASTM D256, respectively. The results are shown in Table IV. As is clear from the values shown in Table IV, the nylon 66 compositions containing about 7% by weight to about 30% by weight of the triguanamine have good flame retardation and Izod impact strength. When the amount of the triguanamine is less than about 5% by weight, the flame retardation is not so effective. On the other hand, when the amount is higher than about 50% by weight, the impact strength of the nylon 66 compositions is too low for practical purposes.

cle for a burning test. The article thus obtained was subjected to the horizontal burning test according to UL Standard Subject 94. The results are shown in Table V.

Table V

| No. | Amount of Triguanamine (g/100g of polyacetal) | UL Standard Subject 94 Horizontal Burning Test | |
|---|---|---|---|
| | | Rate of Burning (nm/minute) | Judgment |
| Comparative Example 5 | 0 | 59 | HB |
| Example 8 | 11 | 30 | HB |
| 9 | 33 | Selfextinguishing | V-2* |

*In accordance with UL Standard Subject 94 vertical burning test.

Table IV

| No. | Amount of Triguanamine (g/100 of nylon 66) | UL Standard Subject 94 Vertical Burning Test | | | Izod Impact Strength (Kg-cm/cm) |
|---|---|---|---|---|---|
| | | Time of Burning (second) | Inflamation of Absorbent Cotton by Burnt Drop | Judgment | |
| Comparative Example 2 | 0 | 6.9 | Occurred | V-2 | 4.5 |
| 3 | 1 | 6.3 | " | " | 4.6 |
| Example 4 | 7 | 1.2 | " | " | 4.4 |
| 5 | 11 | 0.3 | None | V-0 | 4.0 |
| 6 | 25 | 0.1 | " | " | 3.2 |
| 7 | 67 | 0.0 | " | " | 1.9 |
| Comparative Example 4 | 150 | 0.0 | " | " | 0.2 |

EXAMPLES 8 TO 9 and

COMPARATIVE EXAMPLE 5

The same dry pellets of polyacetal resin as in Example 2, Run No. 18 were mixed with the triguanamine obtained in Example 1 in a ratio as set forth in Table V, and the resulting mixture was melt mixed and molded in the same manner as in Example 2 to give a shaped arti- While the invention has been described in detail and with reference to specific embodiments thereof, it will be apparent to one skilled in the art that various changes and modifications can be made therein without departing from the spirit and scope thereof.

What is claimed is:

1. 1,3,6-Tris(4,6-diamino-1,3,5-triazine-2-yl)hexane.

* * * * *